United States Patent [19]

Harfmann et al.

[11] Patent Number: 5,847,129
[45] Date of Patent: Dec. 8, 1998

[54] PROCESS FOR THE REGENERATION OF AN AQUEOUS PROCESS LIQUID OF THE AMINE-OXIDE PROCESS

[75] Inventors: Peter Harfmann, Regau; Stephan Astegger, Timelkam, both of Austria

[73] Assignee: Lenzing Aktiengesellschaft, Lenzing, Austria

[21] Appl. No.: 843,722

[22] Filed: Apr. 17, 1997

Related U.S. Application Data

[63] Continuation-in-part of PCT/AT96/00151, Aug. 16, 1996, and PCT/AT96/00148, Aug. 16, 1996.

[51] Int. Cl.$^6$ .................................................. C07D 295/24
[52] U.S. Cl. ......................... 544/173; 544/170; 588/215; 588/219; 588/227
[58] Field of Search ................................... 544/170, 173; 588/215, 219, 227

[56] References Cited

U.S. PATENT DOCUMENTS

| | | | |
|---|---|---|---|
| 4,783,502 | 11/1988 | Faler et al. | 524/871 |
| 5,216,154 | 6/1993 | Zimmerman | 544/173 |

FOREIGN PATENT DOCUMENTS

| | | |
|---|---|---|
| 092862 | 11/1983 | European Pat. Off. . |
| 254803 | 2/1988 | European Pat. Off. . |
| 320690 | 6/1989 | European Pat. Off. . |
| 356419 | 2/1990 | European Pat. Off. . |
| 401503 | 12/1990 | European Pat. Off. . |
| 553070 | 7/1993 | European Pat. Off. . |
| 8808039 | 12/1989 | France . |
| 259863 | 9/1988 | Germany . |
| 4140259 | 6/1993 | Germany . |
| 93/02965 | 2/1993 | WIPO . |
| 97/07268 | 2/1997 | WIPO . |

OTHER PUBLICATIONS

Shuker et al., Anal. Chem. vol. 55, No. 13, pp. 2152–2155 (1993) (Abstract).

Rhighezza et al., J. Chromat, 1987 vol. 410, pp. 145–155 (1987).

Conboy et al., Analyst, vol. 114, No. 2, pp. 155–159 (1989, London) (Abstract).

Buechele et al. J. Anal. Chem., vol. 336, No. 4, pp. 328–332 (1990) (Abstract).

*Primary Examiner*—Peter O'Sullivan
*Attorney, Agent, or Firm*—Baker & Botts LLP

[57] ABSTRACT

The invention is concerned with a process for the destruction of N-nitrosomorpholine in an aqueous solution containing N-nitrosomorpholine and a peroxidic oxidant, characterized in that said aqueous solution is exposed to ultraviolet radiation having a wavelength of substantially 254 nm.

12 Claims, 1 Drawing Sheet

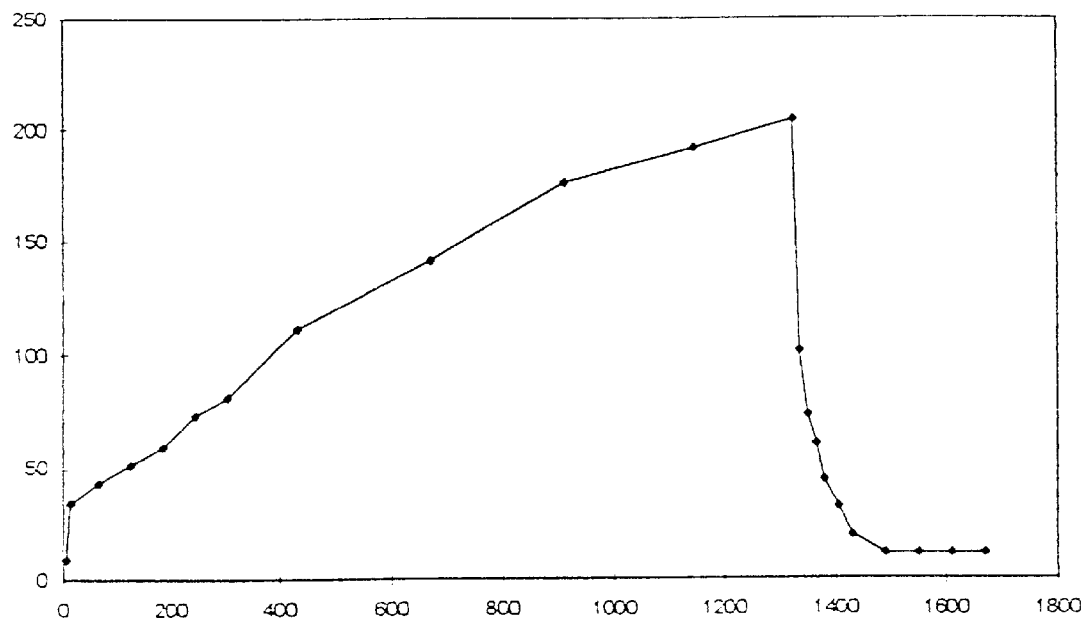

PROCESS FOR THE REGENERATION OF AN AQUEOUS PROCESS LIQUID OF THE AMINE-OXIDE PROCESS

CROSS REFERENCE TO RELATED APPLICATIONS

The application is a continuation-in-part of PCT/AT96/00151, Aug. 16, 1996, and PCT/AT96/00148, Aug. 16, 1996, both of which are incorporated by reference herein.

INTRODUCTION

The present invention is concerned with a process for the regeneration of an aqueous process liquid of the amine-oxide process wherein N-nitrosomorpholine is destroyed. In particular, the present invention is concerned with a process for the regeneration of an aqueous process liquid of the amine-oxide process containing N-nitrosomorpholine and a peroxidic oxidant.

BACKGROUND OF THE INVENTION

For some decades there has been searched for processes for the production of cellulose moulded bodies able to substitute the viscose process, today widely employed. As an alternative which is interesting for its reduced environmental impact among other reasons, it has been found to dissolve cellulose without derivatisation in an organic solvent and extrude from this solution moulded bodies, e.g. fibres, films and other moulded bodies. Fibres thus extruded have received by BISFA (The International Bureau for the Standardization of man made fibers) the generic name Lyocell. By an organic solvent, BISFA understands a mixture of an organic chemical and water.

It has turned out that as an organic solvent, a mixture of a tertiary amine-oxide and water is particularly appropriate for the production of cellulose moulded bodies. As the amine-oxide, primarily N-methylmorpholine-N-oxide (NMMO) is used, other amine-oxides are described e.g. in EP-A-0 553 070. A process for the production of mouldable cellulose solutions is known e.g. from EP-A-0 356 419. For the purposes of the present specification and the present claims, the production of cellulose moulded bodies using tertiary amine-oxides generally is referred to as amine-oxide process.

In EP-A-0 356 419, an amine-oxide process for the production of spinnable cellulose solutions is described, wherein as a starting material among other substances a suspension of cellulose in liquid, aqueous N-methylmorpholine-N-oxide (NMMO) is used. This process consists in transforming the suspension in a thin-film treatment apparatus in one single step and continuously into a mouldable solution. Finally, the mouldable solution is spun into filaments by means of a forming tool such as a spinneret and the filaments are conducted through a precipitation bath.

In the precipitation bath the cellulose is precipitated. The tertiary amine-oxide is accumulated in the precipitation bath. The precipitation bath may contain up to 30 weight % of amine-oxide. For economic reasons of the amine-oxide process it is of vital importance to recover the amine-oxide as completely as possible and reuse it for the production of a mouldable cellulose solution. Thus is necessary to recover NMMO from the precipitation bath.

However, in addition to the amine-oxide degradation products of the amine-oxide are also accumulated in the precipitation bath. These degradation products may be intensively coloured, thus deteriorating the quality of the cellulose moulded bodies produced, on the other hand, other substances may additionally represent a safety risk, since under certain conditions the amine-oxide tends to show highly exothermic decomposition reactions and these decomposition reactions may be induced or accelerated by certain substances. These substances have to be removed from the precipitation bath which is to be regenerated before the NMMO is concentrated and separated in accordance with the purification process described in WO 97/07268.

After removing these unwanted substances, water is withdrawn from the purified precipitation bath which optionally is combined with other process liquids of the amine-oxide process such as vapour condensates formed during the production of the cellulose solution. This may be carried out for instance by means of evaporation. The residue of this evaporation contains highly concentrated aqueous amine-oxide which is recycled again into the amine-oxide process. The vapours of the evaporation consist mainly of water, wherein significant amounts of N-methylmorpholine, the main degradation product of NMMO, are also dissolved. Moreover, the vapours contain also NMMO and morpholine. Typically, the vapours contain up to 100 mg of NMMO, 240 mg of N-methylmorpholine and 30 mg of morpholine per liter. Conveniently, these vapours are concentrated, e.g. by means of reverse osmosis. The aqueous solution obtained contains typically up to 4 g of NMMO, up to 10 g of N-methylmorpholine and up to approximately 1 g of morpholine.

To keep the NMMO losses as low as possible, it is tried to reoxidize the N-methylmorpholine to NMMO. This may be achieved for instance by means of a peroxidic oxidant. A disadvantage however is that the morpholine present in the process liquid introduced as an impurity together with the tertiary amines is partially transformed into toxic N-nitrosomorpholine, which is accumulated unwontedly in the NMMO cycle.

A process for the preparative production of tertiary amine-oxides by means of oxidation of tertiary amines is known e.g. from EP-A-0 092 862. According to this process, the amine-oxide is oxidized under pressure with molecular oxygen in an aqueous solvent, said solvent having a pH value approximately equal to or higher than the pKa value of the tertiary amine.

DD-A-259 863 is concerned with the production of aqueous NMMO solutions by means of oxidation of N-methylmorpholine with $H_2O_2$ and by passing the reaction solution through one or more exchanger columns filled with styrene/divinylbenzene copolymer containing sulfonate groups, as well as by adjusting the pH value of the solution to values ranging from 8 to 5 by addition of phosphoric acid.

Oxidation of N-methylmorpholine with $H_2O_2$ to produce NMMO is known e.g. from EP-A-0 254 803. From DE-A-0 414 0259, the production of NMMO by a process is known wherein the formation of nitrosamines is restricted by scavenging primary and secondary amines, for instance by means of acid halides.

EP-A-0 320 690 describes the production of amine-oxides substantially free from nitrosamines by oxidation with peroxides in the presence of a combination of $CO_2$/ascorbic acid acting as a nitrosamine inhibitor. From EP-A-0 401 503, oxidation with $H_2O_2$ in water and a co-solvent, preferably a carboxylic acid ester, is known. According to FR-A-8 808 039, oxidation is carried out during addition of $CO_2$, and according to U.S. Pat. No. 5,216,154, oxidation to NMMO is carried out in a pure $CO_2$ atmosphere.

In the state of the art, the formation of nitrosamine either is not prohibited, or it is achieved by removing the starting products of the N-nitrosomorpholine or by using additives to slow down the formation rate of the N-nitrosomorpholine. Particularly in an amine-oxide process comprising a closed cycle, the addition of various chemicals such as acid halides or ascorbic acid or $CO_2$ to the process causes problems in the purification of the process liquids, since the degradation products introduced together with the added chemicals have to be removed from the process. For many chemicals, it is also necessary to consider safety aspects such as the risk of exothermic reactions. Thus, neither of the described processes is appropriate for the regeneration of process liquids of the amine-oxide process.

BRIEF SUMMARY OF THE INVENTION

Thus it is the object of the present invention to provide a process for the destruction of nitrosomorpholine in an aqueous solution containing N-nitrosomorpholine and a peroxidic oxidant, said process destroying efficiently N-nitrosomorpholine without addition of chemicals and restricting its accumulation in the solution. It is another object of the present invention to provide a process for the regeneration of process liquids, wherein the toxic N-nitrosomorpholine is removed to a large degree in a simple way and N-methylmorpholine is oxidized to a great extent to NMMO.

BRIEF DESCRIPTION OF THE DRAWINGS

A preferred embodiment of the invention is illustrated in the appended drawings in which FIG. 1 is a graphical representation of the content of N-nitrosomorpholine in a solution exposed to ultraviolet radiation in accordance with the invention.

DETAILED DESCRIPTION OF THE INVENTION

In a process for the destruction of nitrosomorpholine in an aqueous solution containing N-nitrosomorpholine and a peroxidic oxidant, this objective is attained according to the invention by means of exposing the aqueous solution to ultraviolet radiation having a wavelength of substantially 254 nm. The exposure rate may range e.g. from 200 to 500 $mJ/cm^2$, depending on the design of the lamp and the process conditions, particularly the temperature. The process according to the invention does not involve any additional chemicals.

It has been shown that the exposure according to the invention allows a highly efficient destruction of the Nitrosomorpholine and that the presence of the peroxidic oxidant does not interfere.

General methods for the quantitative analysis of nitrosamines which use a UV exposure and a subsequent determination of the nitrites formed are known (D. E. G. Shuker, S. R. Tannenbaum, Anal. Chem., 1983, 55, 2152–2155; M. Rhighezza, M. H. Murello, A. M. Siouffi, J. Chromat., 1987, 410, 145–155; J. J. Conboy, J. H. Hotchkiss, Analyst, 1989, 114, 155–159; B. Buchele, L. Hoffmann, J. Lang, Fresen.J.Anal.Chem., 1990, 336, 328–333). These analytic methods however do not deal with the destruction of N-nitrosomorpholine.

The ultraviolet light to which the aqueous solution is exposed is best emitted from a mercury low-pressure lamp. These low-pressure lamps have an intensity maximum at 254 nm.

For exposure according to the invention using a low-pressure lamp, the lamp may be hung into a container containing the process liquid which is to be treated. However the lamp may also be arranged in another way. Moreover, exposure may be carried out for instance during a continuous recycling of the solution to be exposed in a thin-film UV-reactor.

The invention is further concerned with a process for the production of an aqueous solution of N-methylmorpholine-N-oxide, characterized by the following steps:

(a) providing an aqueous solution containing N-methylmorpholine and morpholine;

(b) treating said aqueous solution with a peroxidic oxidant to oxidize N-methylmorpholine to N-methylmorpholine-N-oxide, and (c) exposing the aqueous solution to ultraviolet radiation emitted from a mercury low-pressure lamp.

The exposure is preferably carried out either during the treatment with the peroxidic oxidant or subsequently to it.

As the peroxidic oxidant, in the process according to the invention preferably $H_2O_2$ is used. $H_2O_2$ is employed preferably as an aqueous solution having 30–50 weight % of $H_2O_2$. $H_2O_2$ is best employed in an amount of from 0.8 to 2 mole per mole of N-methylmorpholine.

A particularly preferred embodiment of the process according to the invention consists in that the pH value of the aqueous solution which is treated with the peroxidic oxidant lies within a range of 6.0 to 9.0. It has been shown that in this range the oxidation of N-methylmorpholine to N-methylmorpholine-N-oxide shows a maximum and the unwanted formation of the N-nitrosomorpholine a minimum. Thus, in combination with an exposure treatment, the content of N-nitrosomorpholine in the recycled aqueous NMMO may be kept particularly low. The adjustment of the pH value may be attained for instance by adding a base.

The invention is further concerned with a process for the regeneration of N-methylmorpholine-N-oxide from a spent precipitation bath produced in the amine-oxide process, characterized by the following steps:

(1) purifying the spent precipitation bath;

(2) evaporating water from the purified precipitation bath, producing a concentrated, aqueous N-methylmorpholine-N-oxide and vapours, said vapours being condensed and containing NMMO, N-methylmorpholine and morpholine;

(3) removing water from the condensed vapours to concentrate the condensed vapours, provided that the water removal is not carried out by means of evaporation;

(4) treating the condensed, concentrated vapours with a peroxidic oxidant to oxidize N-methylmorpholine to N-methylmorpholine-N-oxide, exposing them to ultraviolet radiation emitted by a mercury low-pressure lamp and regenerating them to recover N-methylmorpholine-N-oxide.

Regeneration and recovery of the NMMO may be carried out by condensing the exposed aqueous solution obtained in step (4). Prior, the exposed solution is conveniently combined with other purified precipitation baths. For this reason a closed process is attained.

Moreover, it is possible to carry out oxidation, exposure to ultraviolet radiation and evaporation in a single reaction vessel, each of the operations being carried out more or less simultaneously.

Another possibility consists in removing continuously during the reaction part of the reaction solution from the reaction mixture, passing it across an UV reactor and refeeding it to the reaction vessel.

By means of the following Examples, the invention will be explained in more detail. The abbreviations NMOR, NMMO, NMM and M used in the following denote N-nitrosomorpholine, N-methylmorpholine-N-oxide, N-methylmorpholine and morpholine respectively.

EXAMPLE 1

An aqueous solution containing 42 µg of NMOR, 459 mg of NMMO, 4300 mg of NMM and 200 mg of M per liter was exposed in a UV reactor to a mercury low-pressure lamp (of the Katadyn UV projector EK-36 no. 79000 type made by Katadyn) (wavelength: 254 nm). The temperature of the aqueous solution was 60° C.

The NMOR concentration was determined by means of HPLC (column: Hypersil ODS 250×4 mm; 50° C.; eluant: A=0.6% of acetonitrile; B 49.7% of $H_2O$; gradient 1 ml/min.; 10 min. —100% A; 7 min. 100% B; detector: UV 238 nm).

After an exposure time of 150 minutes, the NMOR content in the process liquid decreased to 40 µg/l. After another 150 minutes, there was no more NMOR to be found.

After there was no more detection of NMOR, the exposure was finished and in intervals of several hours the process liquids were analyzed to detect any NMOR. There was no detection of NMOR, thus being proved that NMOR will not form again.

EXAMPLE 2

An aqueous solution containing 25 µg of NMOR, 2530 mg of NMMO, 3923 mg of NMM and 30 mg of M per liter was mixed with 30% $H_2O_2$ (mole of NMM/mole of $H_2O_2$= 1/1.2) to oxidize NMM to NMMO and exposed to UV radiation as described in Example 1. Within the first 90 minutes, the NMOR concentration increased to 45 µg/l, which is due to a fast reaction of the M present in the solution. Afterwards, the NMOR concentration decreased again rapidly. After 6 hours, there was no detection of NMOR.

After a total oxidation time of 20 hours, the solution contained 5386 mg of NMMO/liter. This amounts to a yield of 62% of theory.

EXAMPLE 3

An aqueous solution containing 1484 mg of NMMO, 3332 mg of NMM and 48 mg of M per liter (NMOR was below the detection limit) was treated with $H_2O_2$ as described in Example 2. At first however it was not exposed to ultraviolet radiation. Thus the NMOR content increased to 44 µg/l during the first hour, and in the course of a total of 21 hours to 205 µg/l. After approximately 21 hours, the solution was exposed to ultraviolet radiation as described in the above Examples. By means of the exposure to ultraviolet radiation according to the invention, the NMOR concentration fell to 12 µg/l within 3 hours.

The results are graphically represented in the FIG. 1 showing a diagram which as the X axis indicates the time in minutes and as the Y axis the content of NMOR in µg/l.

We claim:

1. A process for the destruction of N-nitrosomorpholine in an aqueous solution containing N-nitrosomorpholine and a peroxidic oxidant, comprising the steps of exposing said aqueous solution to ultraviolet radiation.

2. A process according to claim 1, wherein said ultraviolet radiation is emitted by a mercury low-pressure lamp.

3. A process according to claim 1 or claim 2, wherein said peroxidic oxidant comprises $H_2O_2$.

4. A process for the production of an aqueous solution of N-methylmorpholine-N-oxide, comprising the following steps:
   (a) providing an aqueous solution containing N-methylmorpholine and morpholine;
   (b) treating said aqueous solution with a peroxidic oxidant to oxidize N-methylmorpholine to N-methylmorpholine-N-oxide, and
   (c) exposing said aqueous solution to ultraviolet radiation emitted by a mercury low-pressure lamp.

5. A process according to claim 4, wherein step (c) is carried out subsequently to step (b).

6. A process according to claim 4 or claim 5, wherein the pH value of said aqueous solution which is treated with said peroxidic oxidant lies in the range of from 6.0 to 9.0.

7. A process for the regeneration of N-methylmorpholine-N-oxide from a spent precipitation bath produced in the amine-oxide process, comprising the following steps:
   (a) purifying the spent precipitation bath;
   (b) evaporating water from the purified precipitation bath, thereby producing a concentrated, aqueous N-methylmorpholine-N-oxide and vapours, said vapours being condensed and containing N-methylmorpholine-N-oxide, N-methylmorpholine and morpholine;
   (c) removing water from the condensed vapours to concentrate the condensed vapors, wherein the water removal is not carried out by means of evaporation;
   (d) treating the condensed, concentrated vapours with a peroxidic oxidant to oxidize N-methylmorpholine to N-methylmorpholine-N-oxide,
   (e) exposing the condensed, concentrated vapors to ultraviolet radiation emitted by a mercury low-pressure lamp, and
   (f) regenerating the condensed, concentrated vapors to recover N-methylmorpholine-N-oxide.

8. A process according to claim 1, wherein the ultraviolet radiation has a wavelength of substantially 254 nm.

9. A process according to claim 4, wherein step (c) is carried out during step (b).

10. A process according to claim 4, wherein the peroxidic oxidant comprises $H_2O_2$.

11. A process according to claim 10, wherein the peroxidic oxidant is an aqueous solution having 30–50 weight % of $H_2O_2$.

12. A process according to claim 10, wherein the $H_2O_2$ is present in an amount of from 0.8 to 2 mole per mole of N-methylmorpholine.

* * * * *

UNITED STATES PATENT AND TRADEMARK OFFICE
CERTIFICATE OF CORRECTION

PATENT NO. : 5,847,129
DATED : December 8, 1998
INVENTOR(S) : Harfmann, et al

It is certified that error appears in the above-identified patent and that said Letters Patent is hereby corrected as shown below:

ON THE COVER PAGE:

[30] Foreign Application Priority Data
August 18, 1995 [AT]   Austria AT A1401/95
August 18, 1995 [AT]   Austria AT A1400/95

Col. 1, line 22: "has" should read -- have --

Col. 2, line 34: "unwontedly" should read
-- unwantedly --

Col. 3, line 49: "Nitrosomorpholine" should read
-- N-nitrosomorpholine --

Signed and Sealed this

Twenty-eighth Day of March, 2000

Attest:

Q. TODD DICKINSON

Attesting Officer

Commissioner of Patents and Trademarks